US00PP22685P2

(12) United States Plant Patent
Korlipara et al.

(10) Patent No.: US PP22,685 P2
(45) Date of Patent: Apr. 24, 2012

(54) ***HOSTA* PLANT NAMED 'RASPBERRY SUNDAE'**

(50) Latin Name: *Hosta hybrida*
Varietal Denomination: Raspberry Sundae

(75) Inventors: Harini Korlipara, Canby, OR (US); Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,269

(22) Filed: Nov. 10, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt
(74) *Attorney, Agent, or Firm* — Klarquist Sparkman, LLP

(57) ABSTRACT

A new and distinct *Hosta* plant characterized by the combination of creamy white-centered foliage with green margins and strong red petioles and flower stalks. In the spring the red of the petioles shows up in the base of the leaf as well. *Hosta* 'Raspberry Sundae' has a compact habit and attractive violet flowers in late summer into fall.

2 Drawing Sheets

Botanical denomination: *Hosta hybrida.*
Variety designation: 'Raspberry Sundae'.

BACKGROUND OF THE INVENTION

The present invention relates to a new and distinct cultivar of *Hosta,* botanically known as a *Hosta hybrida,* and hereinafter will be referred to by its cultivar name 'Raspberry Sundae'. *Hosta* is in the family *Hostaceae.* The plant is the culmination of a breeding program for variegated, red petiole *Hosta.* It was bred in Canby, Oreg. using unpatented proprietary parents. The exact parents are unknown.

Compared to *Hosta* 'Cherry Berry' (an unpatented plant), *Hosta* 'Raspberry Sundae' has a larger habit, larger and wider leaves, and darker petioles and scape. Compared to other red petiole *Hosta,* the new cultivar is variegated with creamy white centers and green margins rather than not variegated.

SUMMARY OF THE INVENTION

This new cultivar is unique in the combination of creamy white-centered foliage with green margins and strong red petioles and flower stalks. In the spring the red of the petioles shows up in the base of the leaf as well. *Hosta* 'Raspberry Sundae' has a compact habit and attractive violet flowers in late summer into fall.

This new cultivar has been reproduced only by asexual propagation (division and tissue culture). Each of the progeny exhibits identical characteristics to the new cultivar. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant in late spring.
FIG. 2 shows an older flower stalk in late September.

FIG. 3 shows the maturing seed pods in late September.
FIG. 4 shows a close up of the petiole color in late September.

DETAILED PLANT DESCRIPTION

The following is a detailed description of the new *Hosta* cultivar based on observations of a two-year-old specimen grown in the ground in an open air shade house with 50% shade in Canby, Oreg. in late September. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to 53 cm wide and 23 cm tall from the top of the soil to the top of the foliage.
*Form.*—Clumping to form a mound with leaves cascading downwards.
*Number of crowns per plant.*—About 10.
*Number of leaves per crown.*—5 to 11.

Leaf:

*Type.*—Simple.
*Shape.*—Ovate.
*Arrangement.*—Basal rosette.
*Blade length.*—Grows to 18.5 cm.
*Blade width.*—Grows to 13 cm.
*Margins.*—Entire and somewhat undulate.
*Apex.*—Cirrhose.
*Base.*—Rounded and cupping inwards.
*Petiole.*—13 cm to 17 cm long and 7 mm to 12 mm wide, clasping, glabrous, sulcate, inner surface heavily spotted Greyed Purple N186C, outer surface Greyed Purple N186C except at base where spotted.
*Texture.*—Leathery.
*Surface texture.*—Glabrous on both surfaces, glossy on bottom surface.

*Venation.*—Average of 7 pairs of veins, camptodrome pattern, impressed on upper surface and raised on lower surface.

*Color.*—Topside margins and irregularly along veins from the tip Green N137A, lightening to Green 137A near center, centers Yellow White 158B, base along main vein speckled Greyed Purple N186C; bottom side margins Green 137A and Yellow Green 146C, center Yellow White 158D, base along main vein Greyed Purple N186C.

Inflorescence:

*Type.*—Self cleaning; terminal raceme.

*Number of flowers per raceme.*—About 30.

*Peduncle description.*—Grows to 64 cm long and 6 mm wide, glabrous, Greyed Purple N186C on bottom half to Purple N77A on top half.

*Pedicel description.*—10 mm long and 1 mm wide, glabrous, Violet 86A.

*Floral bracts.*—One at the base of each pedicel, at a 60 degree angle, grows to 5.2 cm long and 16 mm wide, becoming progressively smaller going up the peduncle, ensiform, entire, acuminate, clasping, cupping upward; variegated, bottom side edges Green 137A, center White 155A on top changing to Purple N77C on bottom half; top side margins Green 137A tinted Purple N77C, center White 155A tinted Purple N77A.

*Bloom time.*—August to October in Canby, Oreg.

*Lastingness of inflorescence.*—6 to 8 weeks.

Flower bud:

*Size.*—17 mm long and 7 mm wide.

*Shape.*—Oblong, narrowing at the base.

*Surface texture.*—Glabrous.

*Color.*—Violet Blue 90A.

Flower:

*Type.*—Perfect.

*Shape.*—Campanulate, drooping slightly.

*Size.*—Average 3.5 cm long and 2 cm wide.

*Surface texture.*—Glabrous inside and out.

*Color.*—Outside Violet Blue 91A, inside Violet Blue 90A with edges Violet 91D.

*Corolla description.*—6 overlapping tepals, lobes overlapping, tube 1 cm long and 2 mm wide; outer tepal lobes oblong, entire, obtuse, attenuate, 17 mm long and 8 mm wide; inner tepals obovate, entire, obtuse, attenuate, 17 mm long and 11 mm wide.

*Pistil description.*—35 mm long, ovary 6 cm long and 2 mm wide, Yellow Green 146C, style 3 cm long, White NN155A, stigma White NN155A.

*Stamen.*—6, filaments 2.6 cm long, White NN155A, anthers 3 mm long and 2 mm wide, Greyed Yellow 162A, pollen Yellow 11A.

*Fragrance.*—None.

Fruit:

*Type.*—Capsule.

*Size.*—3 cm long and 7 mm wide.

*Shape.*—Oblong.

*Color.*—Greyed Purple N186C.

Seed: 6 to 10 developed seeds observed per capsule, about 5 mm in length and 3 mm in width, Brown 200A Pest and diseases: Snail and slugs are the main problems on *Hosta*. This new cultivar has leathery waxy leaves and appears to be less appealing to slugs. No susceptibility or resistance to diseases or other pests has been observed.

I claim:

1. A new and distinct hybrid *Hosta* plant as herein shown and described.

* * * * *

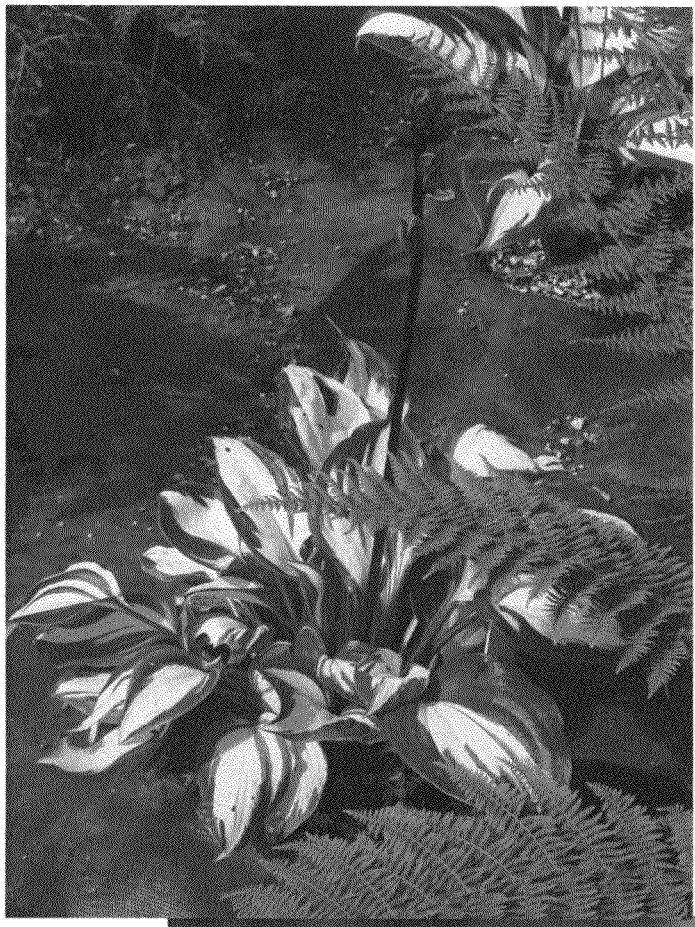
Figure 1 left
Figure 2 below
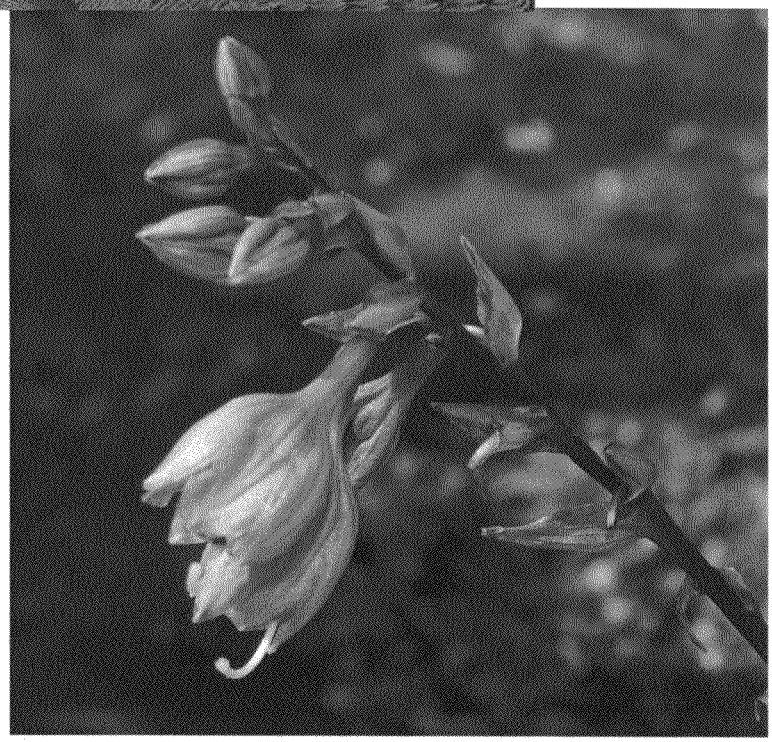

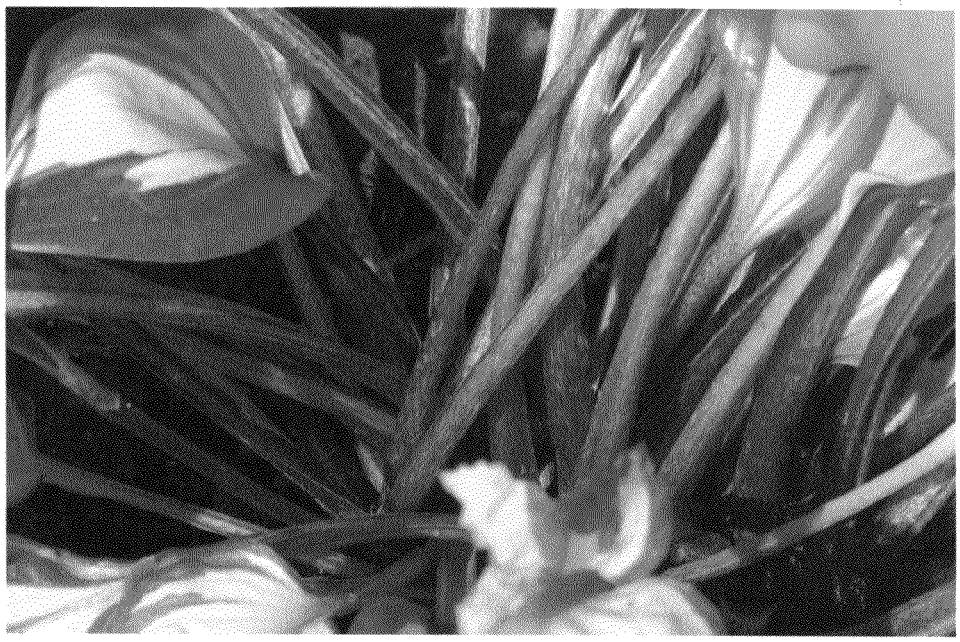

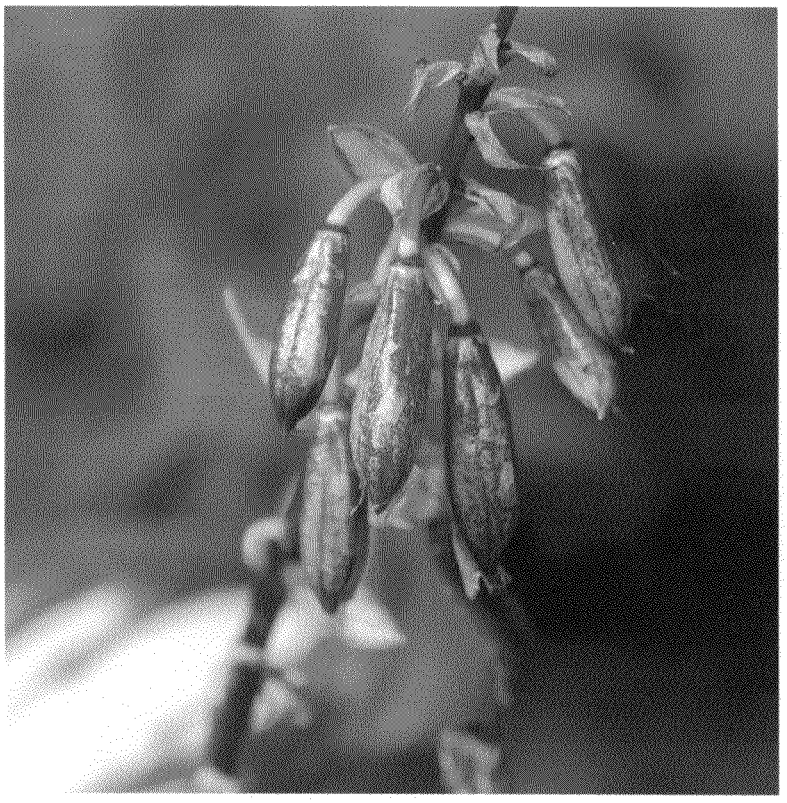
Figure 3 right
Figure 4 below